(12) United States Patent
Rudolf et al.

(10) Patent No.: US 11,814,344 B2
(45) Date of Patent: Nov. 14, 2023

(54) PROCESS FOR THE PREPARATION OF COMPOUNDS WITH AT LEAST ONE ALKYLENE GROUP AND AT LEAST ONE THIOL OR THIOLATE GROUP

(71) Applicant: BASF SE, Ludwigshafen am Rhein (DE)

(72) Inventors: Peter Rudolf, Ludwigshafen (DE); Elliot Christ, Freiburg (DE); Bernd Bruchmann, Ludwigshafen (DE); Indre Thiel, Ludwigshafen (DE); Thomas Maximilian Wurm, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/594,554

(22) PCT Filed: Apr. 23, 2020

(86) PCT No.: PCT/EP2020/061400
§ 371 (c)(1),
(2) Date: Oct. 22, 2021

(87) PCT Pub. No.: WO2020/216873
PCT Pub. Date: Oct. 29, 2020

(65) Prior Publication Data
US 2022/0185773 A1    Jun. 16, 2022

(30) Foreign Application Priority Data

Apr. 26, 2019 (EP) .................................... 19171361

(51) Int. Cl.
*C07C 319/14* (2006.01)
(52) U.S. Cl.
CPC .................. *C07C 319/14* (2013.01)
(58) Field of Classification Search
CPC .................................................. C07C 319/14
See application file for complete search history.

(56) References Cited

U.S. PATENT DOCUMENTS

| 3,232,936 A | 2/1966 | Reynolds |
| 3,326,977 A * | 6/1967 | Johnson ................... G03C 5/39 568/45 |
| 3,624,052 A | 11/1971 | Gobran et al. |
| 6,525,168 B2 | 2/2003 | Zook et al. |

FOREIGN PATENT DOCUMENTS

| CN | 102746476 A | 10/2012 |
| CN | 104395369 A | 3/2015 |
| WO | WO-2019/034470 A1 | 2/2019 |

OTHER PUBLICATIONS

European Search Report for EP Patent Application No. 19171361.9, dated Oct. 14, 2019, 3 pages.
International Search Report for PCT Patent Application No. PCT/EP2020/061400, dated Jul. 13, 2020, 3 pages.
Reybolds, et al., "Mercaptoethylation. I. Mercaptoethylation of Amines with Ethylene Monothiolcarbonate", The Journal of Organic Chemistry, vol. 26, Issue 12, Dec. 1, 1961, pp. 5109-5110.
Zhang, et al., "Poly(thioether)s from Closed-System One-Pot Reaction of Carbonyl Sulfide and Epoxides by Organic Bases", Journal of the American Chemical Society, vol. 141, Issue 13, Mar. 21, 2019, pp. 5490-5496.

* cited by examiner

*Primary Examiner* — Rosalynd A Keys
(74) *Attorney, Agent, or Firm* — Grüneberg and Myers PLLC

(57) ABSTRACT

A process synthesizes a compound with at least one alkylene group and at least one thiol or thiolate group. The process involves reacting a compound with at least one five-membered cyclic monothiocarbonate group with a starter selected from a compound with at least one thiol group, from a compound with at least one hydroxy group, or from a basic inorganic composed; to obtain a compound with at least one alkylene group and at least one thiol or thiolate group and carbon dioxide.

17 Claims, No Drawings

PROCESS FOR THE PREPARATION OF COMPOUNDS WITH AT LEAST ONE ALKYLENE GROUP AND AT LEAST ONE THIOL OR THIOLATE GROUP

CROSS-REFERENCE TO RELATED APPLICATIONS

This application is the National Stage entry under § 371 of International Application No. PCT/EP2020/061400, filed on Apr. 23, 2020, and which claims the benefit of priority to European Application No, 19171361.9, filed on Apr. 26, 2019. The content of each of these applications is hereby incorporated by reference in its entirety.

BACKGROUND OF THE INVENTION

Field of the Invention

The present invention relates to a process for the synthesis of a compound with at least one alkylene group and at least one thiol or thiolate group, wherein
 a compound with at least one five-membered cyclic monothiocarbonate group, shortly referred to as thiocarbonate, is reacted with
 a starter selected from compounds with at least one thiol group, from compounds with at least one hydroxy group or from basic inorganic compounds,
 to obtain a compound with at least one alkylene group and at least one thiol or thiolate group and carbon dioxide.

Description of Related Art

Sulfur compounds and notably sulfur comprising polymers are of interest in many technical applications. The sulfur atom contributes notably to properties such as chemical resistance. Thiol groups are very reactive. Compounds with thiol groups are therefore valuable intermediates in chemical synthesis, and polymers with thiol groups are easily cross-linkable.

Important sulfur comprising polymers are polysulfides. Polysulfides may be obtained by ring-opening polymerization of episulfides, as described in U.S. Pat. No. 3,624,052 for propylene sulfide polymers. In U.S. Pat. No. 6,525,168 B2 a process for the preparation of polysulfides is disclosed, wherein di-halogeno compounds are reacted with dithiols.

From D. D. Reynolds, M. K. Massad, D. L. Fields and D. L. Johnson, Journal of Organic Chemistry, 1961, 5109 to 5110, it is known that cyclic monothiocarbonates may react with a primary amine under decarboxylation to form an amino-substituted ethylene thiol. In a side reaction of the preparation, the ethylene thiol obtained may react with further thiocarbonate under decarboxylation to give a polymer.

U.S. Pat. No. 3,232,936 describes a process for mercaptoethylating amines, especially a process for preparing di-n-butylaminoethylmercaptoethanethiol from a mixture of di-n-butylaminoethanethiol and ethylene monothiocarbonate in toluene.

Cheng-Jian Zhang et al., Journal of the American Society, DOI 10.1021/jacs.9b00544, received Jan. 19, 2019, p. A to G, disclose a closed-system one-pot reaction for the synthesis of polysulfides, wherein carbonyl sulfide (COS) and epoxides are reacted in a closed system to form thiocarbonates as intermediates followed by decarboxylative ring-opening of the thiocarbonates to polysulfides. The process is performed in the presence of an organic base as catalyst.

There is a demand in processes for the synthesis of compounds with thiol groups and notably in polysulfides which are economic and allow an easy preparation of polysulfides with higher functionality.

SUMMARY OF THE INVENTION

Accordingly, a process for the synthesis of a compound with at least one alkylene group and at least one thiol or thiolate group has been found.

The present invention relates to a process for the synthesis of a compound with at least one alkylene group and at least one thiol or thiolate group, wherein a compound with at least one five-membered cyclic monothiocarbonate group, shortly referred to as thiocarbonate, is reacted with a starter selected from compounds with at least one thiol group, from compounds with at least one hydroxy group or from basic inorganic compounds, to obtain a compound with at least one alkylene group and at least one thiol or thiolate group and carbon dioxide.

DETAILED DESCRIPTION OF THE INVENTION

The process of this invention is a process to obtain a compound with at least one alkylene group and at least one thiol or thiolate group.

The alkylene group of the compound obtained corresponds to the two carbon atoms of the five-membered cyclic monothiocarbonate group, preferably to the two carbon atoms of the five-membered cyclic monothiocarbonate group as shown in formula (I), see below; in other words, the alkylene group is notably an ethylene group substituted by $R^1$ to $R^4$, see paragraph above.

In a preferred embodiment, the compound with at least one alkylene group and at least one thiol or thiolate group is a polyalkylenesulfide. The polyalkylenesulfides have at least two alkylene groups and at least one thioether group, preferably at least two thioether groups, and at least one, preferably one thiol or thiolate group, which is usually a terminating thiol or thiolate group. Again, the alkylene groups of the polyalkylenesulfides are preferably ethylene groups substituted by $R^1$ to $R^4$.

To the Thiocarbonate

A five-membered cyclic monothiocarbonate group is a ring system with five members, three of them are from the monothiocarbonate —O—C (=O)—S—, and the further two members are carbon atoms closing the five-membered cycle.

The thiocarbonate may comprise, for example, up to 1000, in particular up to 500, preferably up to 100 five-membered cyclic monothiocarbonate groups.

Suitable thiocarbonates with one or more thiocarbonate groups and the synthesis thereof are described in WO 2019/034470 A1 and WO 2019/034473 A1.

In a preferred embodiment, the thiocarbonate comprises 1 to 10, notably 1 to 5 five-membered cyclic monothiocarbonate groups. In a particularly preferred embodiment, the thiocarbonate comprises 1 or 2 five-membered cyclic monothiocarbonate groups. In a most preferred embodiment, the thiocarbonate comprises 1 five-membered cyclic monothiocarbonate group.

The thiocarbonate may be a polymeric compound with high molecular weight. Preferred thiocarbonates have a molecular weight of up to 10000 g/mol, notably up to 5000 g/mol and particularly up to 1000 g/mol. Most preferred are thiocarbonates having a molecular weight of up to 500 g/mol.

The term "molecular weight", as used herein, means the number average molecular weight Mn, as determined by GPC against polystyrene as standard.

A preferred thiocarbonate is a compound of formula (I)

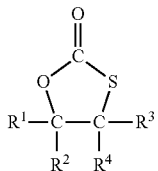

with $R^1$ to $R^4$ independently from each other representing hydrogen or an organic group with up to 50 carbon atoms, whereby, alternatively, $R^2$, $R^4$ and the two carbon atoms of the thiocarbonate ring may also together form a five to ten membered carbon ring.

In case that any of $R^1$ to $R^4$ represent an organic group, such organic group is preferably an organic group with up to 30, more preferably up to 20 carbon atoms. In a further preferred embodiment $R^2$ and $R^4$ do not form a five to ten membered carbon ring together with the two carbon atoms of the thiocarbonate group.

In case that any of $R^1$ to $R^4$ represent an organic group, such organic group may comprise heteroatoms and functional groups. In particular, it may comprise oxygen, sulfur, silicon and chloride. In a preferred embodiment, the organic group may comprise oxygen or chloride.

The term "chloride, as used herein, is the trivial name of a covalently bound Cl atom.

$R^1$ to $R^4$ may comprise oxygen, for example, in form of ether, hydroxy, aldehyde, keto or carboxy groups. In a preferred embodiment, the organic group is an aliphatic organic group with up to 30 carbon atoms which may comprise oxygen, nitrogen or chloride, in particular oxygen.

In a more preferred embodiment, the organic group is selected from an alkyl group, from a group $—CH_2—O—^5$ or a group $—CH_2—O—C(=O)—R^6$ or a group $—CH_2—NR^7R^8$ with $R^5$ to $R^8$ being an organic group with up to 30 carbon atoms, preferably up to 20 carbon atoms. In particular, $R^5$ to $R^8$ represent an aliphatic or aromatic group, which may comprise oxygen, for example, in form of ether groups. In a preferred embodiment, $R^5$ to $R^8$ represent an aliphatic hydrocarbon group, such as an alkyl group with 1 to 10 carbon atoms, an alkoxy group or a poly-alkoxy group. In a most preferred embodiment, $R^5$ to $R^8$ represent an aliphatic hydrocarbon group, in particular an alkyl group with 1 to 10 carbon atoms.

In a preferred embodiment, the organic group is a group $—CH_2—O—R^5$ or a group $—CH_2—O—C(=O)—R^6$.

Preferably, two to four groups of $R^1$ to $R^4$ in formula (I) represent hydrogen, and the remaining groups $R^1$ to $R^4$ represent an organic group.

Most preferably, three of $R^1$ to $R^4$ in formula (I) represent hydrogen, and the remaining group of $R^1$ to $R^4$ represents hydrogen or an organic group, preferably an organic group with up to 20 carbon atoms. In a preferred embodiment $R^1$ or $R^2$ is the remaining group representing hydrogen or an organic group. Most preferably, $R^1$ is the remaining group representing hydrogen or an organic group.

A particularly preferred compound of formula (I) is a compound, wherein $R^2$ to $R^4$ in formula (I) represent hydrogen, and $R^1$ is hydrogen or an organic group selected from an alkyl group or a group $—CH_2—O—R^5$ or a group $—CH_2—O—C(=O)—R^6$ or a group $—CH_2—NR^7R^8$ with $R^5$ to $R^8$ being an $C_1$-$C_{10}$-alkyl group, preferably a $C_4$-$C_{10}$-alkyl group.

A most preferred thiocarbonate is a compound of formula (I), wherein at least three of the groups $R^1$ to $R^4$ are hydrogen, and the remaining group is hydrogen or a $C_1$-$C_4$-alkyl group which is notably a methyl group.

In a most preferred embodiment, the thiocarbonate is a compound of formula (I), wherein $R^1$ is hydrogen or an alkyl group, notably a methyl group, and $R^2$ to $R^4$ are hydrogen.

The term "thiocarbonate" shall include also mixtures of different thiocarbonates.

To the Starter

The starters are selected from compounds with at least one thiol group, from compounds with at least one hydroxy group or from basic inorganic compounds. The starters do not comprise five-membered cyclic monothiocarbonate groups and do not correspond to the compound obtained by ring-opening of five-membered cyclic monothiocarbonate groups under decarboxylation.

In a preferred embodiment, the starter does not comprise amino groups, preferably primary, secondary or tertiary amino groups, more preferably primary or secondary amino groups.

The thiol group and the hydroxy group are, herein for short, commonly referred to as "reactive group".

The compounds with at least one thiol or hydroxy group are commonly shortly also referred to as "reactive compounds".

The reactive compound may comprise, for example, up to 1000, particularly up to 500 and preferably up to 100 reactive groups.

In a preferred embodiment, the reactive compound comprises 1 to 10, notably 1 to 5 reactive groups selected from thiol groups, hydroxy groups or any combination thereof. In a particularly preferred embodiment, the reactive compound comprises 1 or 3 reactive groups selected from thiol groups, hydroxy groups or any combination thereof.

More preferably, the reactive compound comprises at least two reactive groups, notably with 2 to 5, more preferably with 2 to 3 reactive groups; the at least two reactive groups may be thiol groups, hydroxy groups or any combination thereof. In a most preferred embodiment, at least one of the at least two reactive groups is a thiol group.

The reactive compound may be a polymeric compound with high molecular weight. Preferred reactive compounds have a molecular weight of up to 10000 g/mol, notably up to 5000 g/mol and particularly up to 1000 g/mol. Most preferred are reactive compounds having a molecular weight of up to 500 g/mol.

The reactive group may also be obtained in situ, for example, in case of compounds with masked reactive groups or compounds comprising a precursor of the reactive group. The masked reactive group or precursor may be transformed into the reactive group in situ during the reaction.

Reactive compounds with thiol groups are, for example, mono thiols or dithiols, such as methylmercaptan or ethylmercaptan; ethanedithiol; butanedithiol; (ethyleneglycol-dimercaptopropylate); benzenedimethanethiol (isomers); 1,8-dimercapto-3,6-dioxaoctane; 2,3-dimercaptopropanol; 2,3-dimercapto-1-propane-sulfonic acid (sodium salt); dimercaptosuccinic acid (salt); 2,2'-thiodiethanethiol; [1,1'-biphenyl]-4,4'-dimethanethiol; dimercaptopropyl laurate; 2,2'-dimercaptoethyl-ether; 3,3'-dimercaptopropyl ether; dimercaptobenzene (isomers); biphenyl-dithiol; terphenyldithiol, or bi-thiophenyl sulfide (4,4-thiobisbenzenethiol);

compounds with more than two thiol groups such as tri/tetra/oligo-thiols, for example, 1,2,3-trimercaptopropane; 2,3-bis[(2-mercaptoethyl)thio]-1-propanethiol; trimethylolpropane-tris-3-mercaptopropionate; pentaerythritol-tetrakis(3-mercaptopropionate); trimercaptotriazine; or Capcure®-type mercaptanes;

compounds with thiol groups and hydroxy groups, such as mercaptoalcohols, for example, mercaptoethanol, mercaptoglycerol, or mercaptophenol;

compounds that comprise other functional groups than reactive groups, such as 3-trialkoxy-silyl-propylthiol, or allylmercaptan.

Thus, preferably, a compound with at least one thiol group, used as a starter, is selected from the group consisting of methylmercaptan, ethylmercaptan; ethanedithiol; butanedithiol; (ethyleneglycol-dimercaptopropylate); benzenedimethanethiol; 1,8-dimercapto-3,6-dioxaoctane; 2,3-dimercaptopropanol; 2,3-dimercapto-1-propanesulfonic acid (sodium salt); dimercaptosuccinic acid (salt); 2,2'-thiodiethanethiol; [1,1'-biphenyl]-4,4'-dimethanethiol; dimercaptopropyl laurate; 2,2'-dimercaptoethyl-ether; 3,3'-dimercaptopropyl ether; dimercaptobenzene (derivatives); biphenyldithiol; terphenyldithiol, or bi-thiophenyl sulfide; 1,2,3-trimercaptopropane; 2,3-bis[(2-mercaptoethyl)thio]-1-propanethiol; trimethylolpropane-tris-3-mercaptopropionate; pentaerythritol-tetrakis(3-mercaptopropionate); trimercaptotriazine; Capcure®-type mercaptanes;

mercaptoethanol, mercaptoglycerol, or mercaptophenol; 3-trialkoxysilyl-propylthiol and allylmercaptan.

Preferred compounds are compounds of formulae

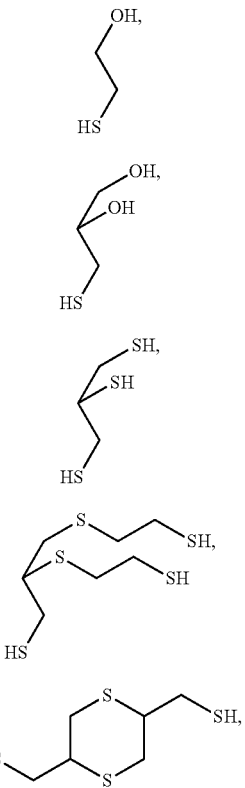

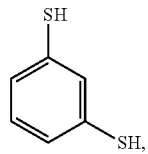

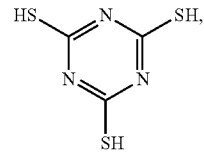

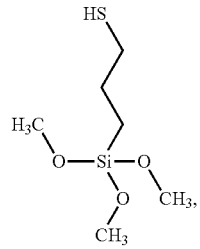

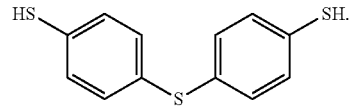

Reactive compounds with hydroxy groups are, for example, compounds with one or two hydroxy groups, for example, $C_1$-$C_{20}$-alkanols, alkanediols such as ethylene glycol, propane-1,2-diol, propane-1,3-diol, butane-1,3-diol, butane-1,4-diol, pentane-1,5-diol, neopentyl glycol, bis (hydroxymethyl)cyclohexanes such as 1,4-bis(hydroxymethyl)-cyclohexane, 2-methylpropane-1,3-diol, methylpentanediols, phenol, thiodiglycol, bisphenol A;

compounds with more than two hydroxy groups, for example, alkanetriols or carbohydrates;

compounds with hydroxy groups and thiol groups, as listed above, such as mercaptoalcohols, for example, mercaptoethanol, mercaptoglycerol, or mercaptophenol;

compounds with at least one hydroxy group and other functional groups such as a vinylether group, or an allylether group or a halogen group;

compounds with higher molecular weight such as, for example, di- or polyetherpolyols, di- or polyesterpolyols or polymers obtained by (co)polymerization of ethylenically unsaturated compounds with hydroxy groups or polyphenols;

Preferred di- or polyesterpolyols have two to eight, preferably two to five hydroxy groups, more preferably two or three, in particular two hydroxy groups and are obtainable by reacting polyols, notably diols, with polycarboxylic acids, notably dicarboxylic acids.

Preferred di- or polyetherpolyols have two to eight hydroxy groups, preferably two to five hydroxy groups, most preferably two hydroxy groups and are obtainable in particular by polymerizing ethylene oxide, propylene oxide, butylene oxide, tetrahydrofuran, styrene oxide or epichlorohydrin with itself, in the presence of a catalyst. Particularly preferred di- or polyetherpolyols are diethylene glycol, triethylene glycol, tetraethylene glycol, polyethylene glycol, dipropylene glycol, polypropylene glycol, and dibutylene glycol and polybutylene glycols.

The starter may also be a basic inorganic compound, preferably a basic inorganic salt. Examples for such compounds are basic zeolites, metal oxides, metal hydroxides and metal sulfides, hydrotalcite, basic clays, and alkaline salts, including alkaline salts supported on oxides or resins.

In a preferred embodiment, the basic inorganic compound is selected from inorganic salts such as metal hydroxides, metal sulfides, metal hydrogen sulfides, metal oxides, metal phosphates and metal silicates. The term "sulfide" includes mono-, oligo- and polysulfides of formula $(S_x)^{2-}$ with x being an integral number of at least 1. The term "hydrogensulfides" includes mono-, oligo- and polyhydrogensulfides of formula $(HS_x)^{1-}$ with x being an integral number of at least 1.

Particularly preferred are metal hydroxides, metal sulfides and metal hydrogensulfides.

The cation of the inorganic salt is preferably a cation with one or two positive charges, as, for example, an alkali or earth alkali cation. Most preferred is an alkali cation such as sodium or potassium.

Examples of preferred inorganic salts are NaOH, $Na_2S$, $K_2S_x$ with x being 1 to 10.

Preferred starters are inorganic basic compounds and reactive compounds with at least two reactive groups, notably with 2 to 5, more preferably with 2 to 3 reactive groups; the at least two reactive groups may be thiol groups, hydroxy groups or any combination thereof. In a more preferred embodiment, at least one of the at least two reactive groups is a thiol group.

Most preferred starters are reactive compounds with at least two reactive groups, notably with 2 to 5, more preferably with 2 to 3 reactive groups; the at least two reactive groups may be thiol groups, hydroxy groups or any combination thereof. In a particularly preferred embodiment, at least one of the at least two reactive groups of the reactive compound is a thiol group.

To the reaction of the starter with the thiocarbonate

The following reaction schemes exemplarily show the reaction for specific starters and the thiocarbonate of formula (I) with Z being an alkyl group and X being the residual chemical group of the starter.

A starter with a thiol group reacts with the thiocarbonate under decarboxylation as follows:

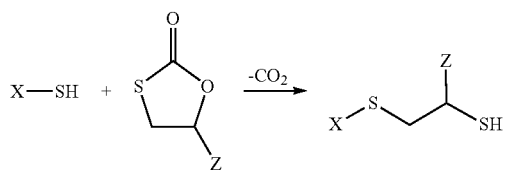

The obtained compound may react with an integral number n of further thiocarbonate under decarboxylation to form a polyalkylenesulfide:

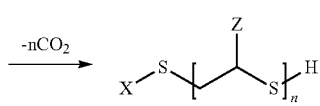

Accordingly, a starter with a hydroxy group reacts with the thiocarbonate under decarboxylation as follows:

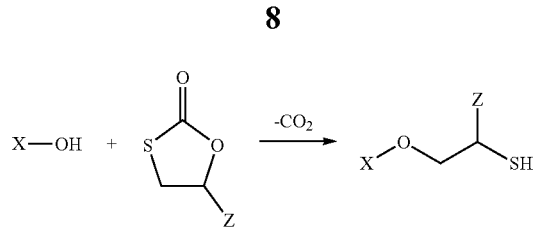

Again, the obtained compound may react with an integral number n of further thiocarbonate under decarboxylation to form a polyalkylenesulfide:

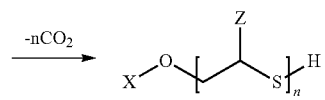

In the above reactions structural isomers of the products may be obtained. The above reaction schemes show only one of the two structural isomers. In the second structural isomer the other carbon of the ethylene group (in other words: the carbon atom adjacent to the oxygen or sulfur of the starter) is substituted by the alkylene group "Z". Usually, the product obtained from the first decarboxylation or after any further decarboxylation comprises more than 60% by weight of the structural isomer as shown above.

Structural isomers which are usually less obtained are, for example, of formula

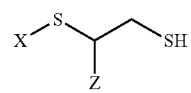

Inorganic salts as starters also cause ring opening and decarboxylation of the thiocarbonate and give compounds with at least one alkylene group and at least one thiol or thiolate group.

Preferably, the hydroxy or thiol groups of the starter are transferred into the respective alkoxylate or thiolate groups before the reaction or by a catalyst used in the reaction.

In a preferred embodiment, the reaction of starters with reactive groups (reactive compounds) and thiocarbonates is performed in the presence of a basic catalyst which forms a salt comprising the alcoholate anion or the thiolate anion derived from the starter.

Suitable catalysts are notably basic catalysts, such as compounds with a tertiary amino group, a guanidino group, an amidine group or a phosphine group, or basic metals salts such as, for example, metal hydroxides and metal sulfides. The catalyst may be added before or during the reaction.

The molar ratio of the reactive groups or of the inorganic salt to the thiocarbonate determines the molecular weight of the obtained product, as is obvious from the above reaction schemes. Usually, the obtained product is a mixture of compounds with different chain length and thus different molecular weight.

In case of starters with both, hydroxy groups and thiol groups, the thiol groups tend to react first. Any selectivity regarding the thiol group can be augmented or damped by selecting suitable conditions and/or starting materials. A hydroxy group of low reactivity will usually promote the selectivity with respect to the thiol group while a less reactive (hindered) thiol group will favor a hydroxy group.

Selecting a highly reactive thiocarbonate will usually suppress, preferably might suppress, any selectivity with respect to the thiol group.

The term "hydroxy group with low reactivity", as used herein, means a hydroxy group which reactivity is lower than a corresponding thiol group.

The reaction may, for example, be performed at temperatures of from −20 to 250° C., preferably between 20 and 100° C. Alternatively, any activation energy for the reactions may be provided by high-energy radiation such as visible or UV light. Usually, the reaction occurs at 20 to 100° C. without any further activation.

A solvent may be used in the reaction. The use of a solvent may be helpful, in case that at least one of the compounds used is solid at room temperature (about 20-25°) and the other starting materials do act already as solvent for the solid compound. Suitable solvents are, for example, toluene, tetrahydrofuran and dimethylformamide. It is an advantage of the process that usually no additional solvent, preferably organic solvent, is required as the starting materials are usually liquid or at least one of the starting materials serves as solvent for any solid starting materials. If the starting materials are solid at room temperature, the reaction may be performed at temperatures above the melting point of any solid starting materials.

Accordingly, a process for the synthesis of a compound with at least one alkylene group and at least one thiol or thiolate group is preferred, wherein a compound with at least one five-membered cyclic monothiocarbonate group is reacted with a starter selected from a compound with at least one thiol group, from a compound with at least one hydroxy group or from a basic inorganic compound, to obtain a compound with at least one alkylene group and at least one thiol or thiolate group and carbon dioxide, wherein a solvent is not required.

The whole amount of thiocarbonate used may be added to the reaction mixture in advance. If mixtures of different thiocarbonates are added, copolymers will be obtained. The thiocarbonate may also be added continuously or in certain increments during the reaction. As the consumption in the reaction follows the sequence of adding the thiocarbonates, block-copolymers or other defined copolymers may be formed from different thiocarbonates added.

From the product mixture obtained, the catalyst may be removed by suitable means, such as washing with water or an aqueous solution of acids such as hydrogen chloride.

To the Compounds Obtained

The compound obtained by the process is a compound with at least one alkylene group and at least one thiol or thiolate group. The thiol or thiolate group is the terminating group of the respective chain, see reaction schemes above. The possibility to have a terminating thiolate group is due to the preferred presence of the catalyst. In case of starters with several reactive groups, several terminating thiol groups, respectively thiolate groups are formed accordingly.

It is an advantage of the reaction that a compound with at least two functional groups may be obtained.

The at least two functional groups may be at least two thiol groups, respectively two thiolate groups if a starter with at least two reactive groups is used.

The at least two functional groups may be at least one thiol, respectively one thiolate group and a further functional group that was part of the starter but was not affected by the reaction. Such functional group could be a hydroxy group of the starter with low reactivity or any other functional group such as alkoxy groups, amino groups or unsaturated groups, for example, vinyl groups, allyl groups, notably vinylether groups.

The product of the reaction may be further reacted with a compound with at least one group that reacts with a thiol group —SH, shortly referred to as SH-reactive compound. Examples of SH-reactive compounds are, for example, mentioned in the non-published patent application PCT/EP2020/053083.

Alternatively or in addition, the product of the reaction may be further reacted with a compound comprising at least one group that reacts with a further functional group of the starter.

The process of the invention is an easy and economic process, performed in one highly selective reaction step. The process does not involve the handling of hazardous compounds such as COS. The process provides an easy access to variety of polyalkylenesulfides and allows the synthesis of copolymers, including block-copolymers, of a desired, predetermined structure and allows control over end group functionality. Furthermore, the process of this invention offers broad possibilities in synthesis as the direct products of the process may be easily further modified.

EXAMPLES

DBU: Diazabicycloundecene

CTC: Compound of formula (I) wherein $R^1$ to $R^4$ are hydrogen

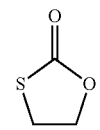

M-CTC: Compound of formula (I) wherein $R^2$ to $R^4$ are hydrogen and $R^1$ is methyl

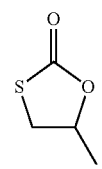

DMP 30: Tris(dimethylaminomethyl)phenol

In each example listed below, a FIGURE shows the starting materials and the product. It is understood that the product is a mixture of structural isomers and polysulfides of different chain length. The FIGURES show the main compound of the mixture of polysulfides obtained, only.

In all examples, the conversion to polysulfides was complete, the starter and the thiocarbonate were fully consumed and reacted to polysulfides without any significant formation of by-products.

Example 1

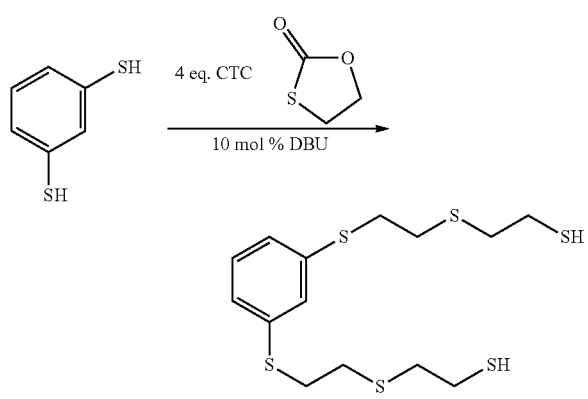

Benzene dithiol (500 mg, 3.52 mmol) and CTC (1456 mg, 14 mmol, 4 eq.) were stirred together at room temperature without any solvents to obtain a homogenous solution. DBU was then added (50 mg, 0.32 mmol), and the reaction was stirred at 60° C. overnight.

Example 2

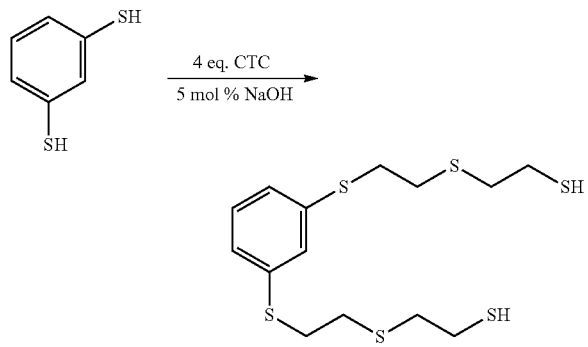

Benzene dithiol (500 mg, 3.52 mmol) and CTC (1456 mg, 14 mmol, 4 eq.) were stirred together at room temperature without any solvents to obtain a homogenous solution. NaOH was then added (10 mg, 0.25 mmol), and the reaction was stirred at 60° C. overnight.

Example 3

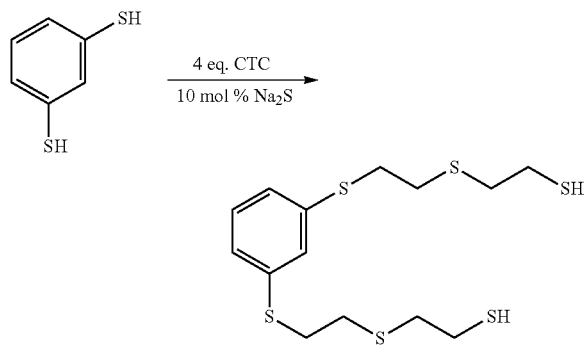

Benzene dithiol (500 mg, 3.52 mmol) and CTC (1456 mg, 14 mmol, 4 eq.) were stirred together at room temperature without any solvents to obtain a homogenous solution. $Na_2S$ was then added (15 mg, 0.20 mmol), and the reaction was stirred at 60° C. overnight.

Example 4

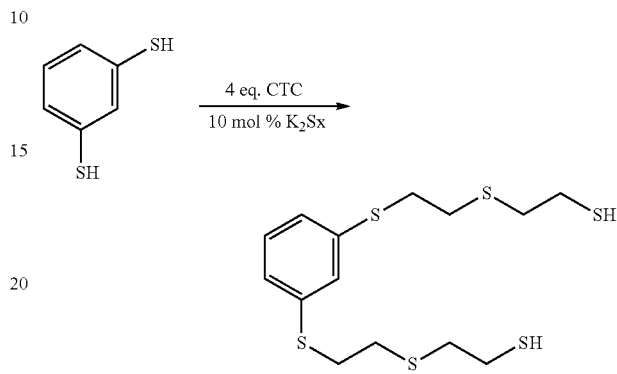

Benzene dithiol (500 mg, 3.52 mmol) and CTC (1456 mg, 14 mmol, 4 eq.) were stirred together at room temperature without any solvents to obtain a homogenous solution. $K_2S_x$ was then added (20 mg, 0.18 mmol), and the reaction was stirred at 60° C. overnight.

Example 5a

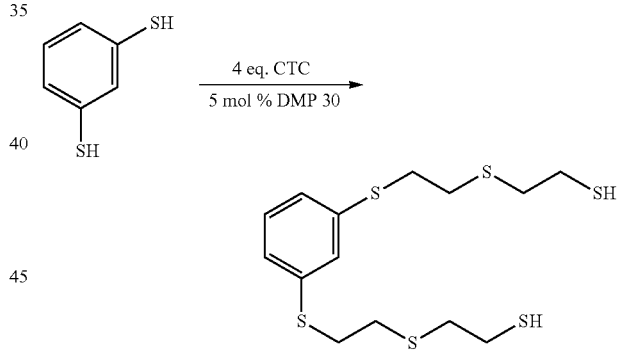

Benzene dithiol (500 mg, 3.52 mmol) and CTC (1456 mg, 14 mmol, 4 eq.) were stirred together at room temperature without any solvents to obtain a homogenous solution. DMP 30 was then added (20 mg, 0.08 mmol), and the reaction was stirred at 60° C. overnight.

Example 5b

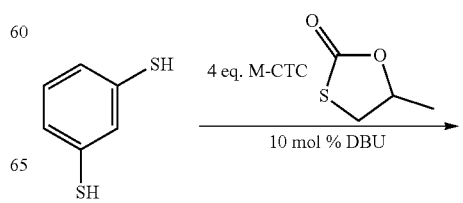

-continued

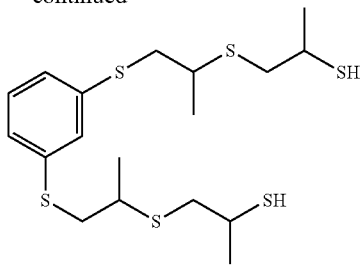

Benzene dithiol (500 mg, 3.52 mmol) and M-CTC (1650 mg, 14 mmol, 4 eq.) were stirred together at room temperature without any solvents to obtain a homogenous solution. DBU was then added (50 mg, 0.32 mmol), and the reaction was stirred at 60° C. overnight.

Example 6

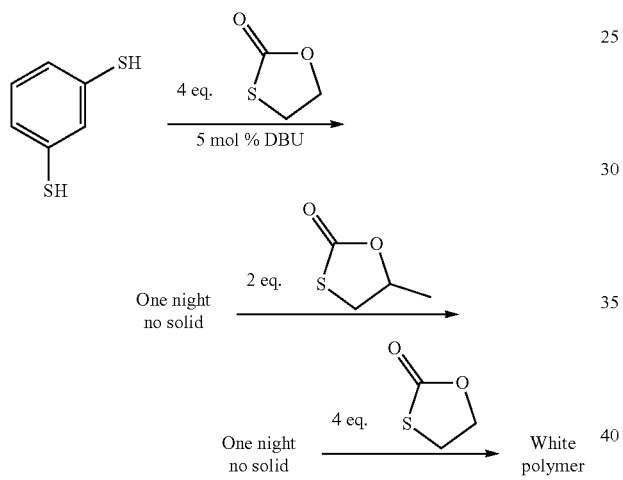

Benzene dithiol (500 mg, 3.52 mmol) and CTC (1456 mg, 14 mmol, 4 eq.) were stirred together at room temperature without any solvents to obtain a homogenous solution. DBU was then added (50 mg, 0.32 mmol), and the reaction was stirred at 60° C. After one night it resulted from GC-MS that all the CTC was consumed, and then M-CTC (825 mg, 7 mmol, 2 eq.) was added to the solution. After another night at 60° C. all of the M-CTC was also consumed, and further CTC (1456 mg, 14 mmol, 4 eq.) was added again. A white polymer was obtained after nearly an hour.

Example 7

-continued

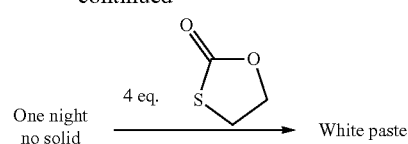

Benzene dithiol (500 mg, 3.52 mmol) and M-CTC (825 mg, 7 mmol, 2 eq.) were stirred together at room temperature without any solvents to obtain a homogenous solution. DBU was then added (50 mg, 0.32 mmol), and the reaction was stirred at 60° C. overnight. After one night it resulted from GC-MS that all the M-CTC was consumed, and then CTC (1456 mg, 14 mmol, 4 eq.) was added to the solution. After a few hours a suspension of a white polymer was obtained.

Example 8

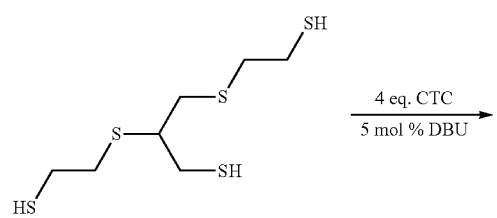 [SMILES: SCCSCC(CS)SCCS]

A liquid polymer has been obtained.

The trimercaptan (500 mg, 1.92 mmol) and CTC (1200 mg, 11.54 mmol, 6 eq.) were stirred together at room temperature without any solvents to obtain a homogenous solution. DBU was then added (25 mg, 0.16 mmol), and the reaction was stirred at 60° C. overnight. The GC-MS showed that all the CTC was consumed.

Example 9

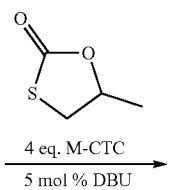
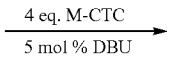

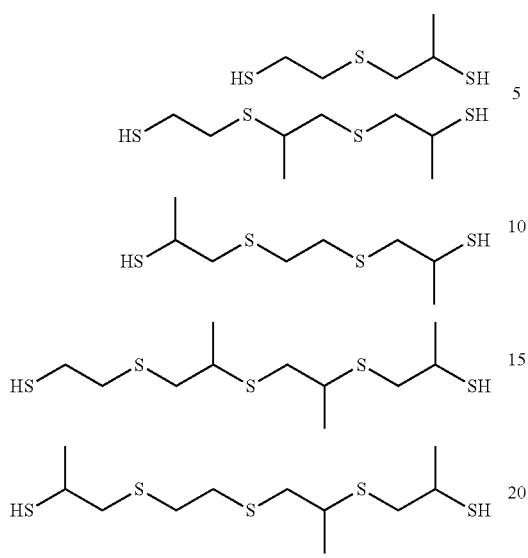
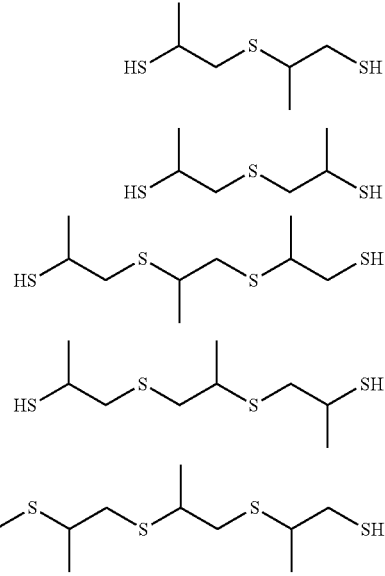

Ethane dithiol (330 mg, 3.51 mmol) and M-CTC (1700 mg, 14.40 mmol, 4 eq.) were stirred together at room temperature without any solvents to obtain a homogenous solution. DBU was then added (25 mg, 0.16 mmol), and the reaction was stirred at 60° C. overnight.

Example 10

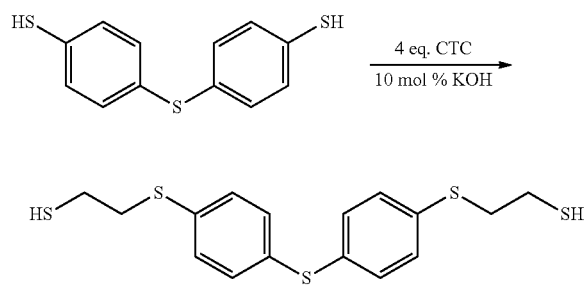

4,4-Thiobisbenzenethiol (500 mg, 2 mmol) and CTC (1456 mg, 14 mmol, 7 eq.) were stirred together at room temperature, KOH (15 mg) was added, and the suspension was stirred at 60° C. overnight. The polyalkylenesulfide of the formula above and corresponding compounds with more ethylene sulfide units were obtained.

Example 11

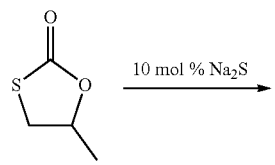

M-CTC (1650 mg, 14 mmol, 4 eq.) and $Na_2S$ (15 mg, 0.20 mmol) were stirred at room temperature without any solvent for 1 hour, and then the reaction mixture was heated at 60° C. overnight.

Example 12

To the unsubstituted thiocarbonate (2 g) solid ground KOH (0.2 g) was added. After stirring the slight suspension for 30 min at 25° C. the reaction mixture turned into a white solid. The solid polymer was insoluble in THF, dichloromethane and ethanol.

Example 13

To the unsubstituted thiocarbonate (2 g) an aqueous solution of KOH (2 g, 15 wt %) was added. After stirring the mixture for 18 hours at 25° C. a white solid precipitated from the biphasic mixture. The solid polymer was insoluble in THF, dichloromethane and ethanol.

Example 14

To the unsubstituted thiocarbonate (2 g) an aqueous solution of $Ca(OH)_2$ (2 g, 15 wt %) was added. After stirring the mixture for 18 hours at 25° C. a white solid precipitated. The white polymer was filtered off and subsequently washed with dichloromethane and acetone.

The invention claimed is:
1. A process for the synthesis of a compound at least one alkylene group and at least one thiol or thiolate group, the process comprising:
reacting a compound with at least one five-membered cyclic monothiocarbonate group with a starter, wherein the starter is selected from the group consisting of a compound with at least one thiol group and a compound with at least one hydroxy group, to obtain the compound with at least one alkylene group and at least one thiol or thiolate group and carbon dioxide,
wherein the at least one five-membered cyclic monothiocarbonate group is a compound of formula (I)

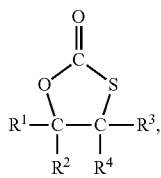

Wherein three of the groups $R^1$ to $R^4$ are hydrogen, and the remaining group is an organic group with up to 20 carbon atoms, or each of the groups $R^1$ to $R^4$ are hydrogen, wherein hydroxy groups or thiol groups of the starter are transferred into respective alkoxylate groups or thiolate groups by a catalyst used in the reaction, and wherein the catalyst is a compound with a tertiary amino group, a guanidino group, an amidine group, or a phosphine group.

2. The process according to claim 1, wherein the starter is a compound with one to three reactive groups selected from the group consisting of a thiol group, a hydroxy group, and a combination thereof.

3. The process according to claim 1, wherein the catalyst is a compound with a tertiary amino group, a guanidino group, or an amidine group.

4. The process according to claim 1, wherein the compound with at least one alkylene group and at least one thiol or thiolate group is a polyalkylenesulfide with at least one terminating thiol group or thiolate group.

5. The process according to claim 1, further comprising:
reacting the compound with at least one alkylene group and at least one thiol or thiolate group with a compound with at least one group that reacts with a thiol group —SH.

6. The process according to claim 1, wherein a solvent is not used in the process.

7. The process according to claim 1, wherein the starter does not comprise an amino group.

8. A process for the synthesis of a compound with at least one alkylene group and at least one thiol or thiolate group, the process comprising:
reacting a compound with at least one five-membered cyclic monothiocarbonate group with a starter, wherein the starter is a compound with at least one thiol group or a compound with at least one hydroxy group, to obtain the compound with at least one alkylene group and at least one thiol or thiolate group and carbon dioxide, wherein the at least one five-membered cyclic monothiocarbonate group is a compound of formula (I)

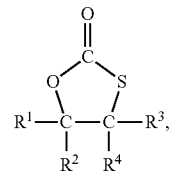

Wherein $R^1$ to $R^4$ independently from each other represent hydrogen or an organic group with up to 50 carbon atoms, alternatively, wherein $R^2$, $R^4$ and the two carbon atoms of the monothiocarbonate ring together form a five to ten membered carbon ring, wherein the thiol group of the starter is transferred into a respective thiolate group by a catalyst used in the reaction, and wherein the catalyst is a compound with a tertiary amino group, a guanidino group, an amidine group, or a phosphine group.

9. The process according to claim 8, wherein the catalyst is a compound with a tertiary amino group, a guanidino group, or an amidine group.

10. The process according to claim 8, wherein each of $R^1$ to $R^4$ represents hydrogen.

11. The process according to claim 8, wherein at least one of $R^1$ to $R^4$ represents an organic group with up to 50 carbon atoms.

12. The process according to claim 9, wherein each of $R^1$ to $R^4$ represents hydrogen.

13. The process according to claim 11, wherein the catalyst is a compound with a tertiary amino group, a guanidino group, or an amidine group.

14. The process according to claim 8, wherein the compound with at least one alkylene group and at least one thiol or thiolate group is a polyalkylenesulfide with at least one terminating thiol group or thiolate group.

15. The process according to claim 1, wherein the catalyst a compound with a guanidino group or an amidine group.

16. The process according to claim 8, wherein the starter is a compound with at least one thiol group.

17. The process according to claim 1, wherein three of the groups $R^1$ to $R^4$ are hydrogen, and the remaining group is an organic group with up to 20 carbon atoms.

* * * * *